United States Patent
Jouhikainen

(10) Patent No.: US 8,693,748 B2
(45) Date of Patent: Apr. 8, 2014

(54) METHOD AND APPARATUS FOR PROCESSING AN INTRAORAL IMAGE

(75) Inventor: Petri Jouhikainen, Jarvenpaa (FI)

(73) Assignee: PaloDEx Group Oy, Tuusula (FI)

( * ) Notice: Subject to any disclaimer, the term of this patent is extended or adjusted under 35 U.S.C. 154(b) by 135 days.

(21) Appl. No.: 13/185,122

(22) Filed: Jul. 18, 2011

(65) Prior Publication Data

US 2012/0183183 A1 Jul. 19, 2012

(30) Foreign Application Priority Data

Jul. 19, 2010 (FI) ...................................... 20105812

(51) Int. Cl.
*G06K 9/00* (2006.01)

(52) U.S. Cl.
USPC ........................................................ 382/128

(58) Field of Classification Search
None
See application file for complete search history.

(56) References Cited

U.S. PATENT DOCUMENTS

| 5,179,579 | A |   | 1/1993 | Dove et al. |
| 5,742,700 | A | * | 4/1998 | Yoon et al. ..................... 382/132 |
| 6,652,141 | B1 | * | 11/2003 | Cianciosi ....................... 378/191 |
| 2003/0026387 | A1 |   | 2/2003 | Makila et al. |
| 2004/0066898 | A1 | * | 4/2004 | Schick et al. ................. 378/98.9 |
| 2006/0212260 | A1 | * | 9/2006 | Kopelman et al. ............ 702/152 |
| 2006/0257816 | A1 |   | 11/2006 | Klemola et al. |
| 2007/0146130 | A1 | * | 6/2007 | Hannemann et al. .... 340/539.22 |
| 2007/0286335 | A1 | * | 12/2007 | De Godzinsky ............... 378/28 |
| 2009/0042168 | A1 | * | 2/2009 | Luo et al. ...................... 433/215 |
| 2009/0238493 | A1 | * | 9/2009 | Crucs ............................ 382/312 |
| 2010/0074401 | A1 | * | 3/2010 | Kayzerman ..................... 378/38 |
| 2010/0177875 | A1 | * | 7/2010 | Steward et al. ............... 378/170 |
| 2010/0189341 | A1 | * | 7/2010 | Oota et al. .................... 382/154 |
| 2011/0008751 | A1 | * | 1/2011 | Pettersson .................... 433/167 |
| 2011/0182406 | A1 | * | 7/2011 | Nelson et al. ................... 378/62 |

FOREIGN PATENT DOCUMENTS

JP 2007050055 A 3/2007

OTHER PUBLICATIONS

Suetens, Paul, "Fundamentals of Medical Imaging", Cambridge University Press, 2005, Chapter Three—Image Operations, pp. 27-43.
Finnish Search Report for parent application FI 20105812, dated Jan. 28, 2011.

\* cited by examiner

*Primary Examiner* — Nirav G Patel
*Assistant Examiner* — Delomia Gilliard
(74) *Attorney, Agent, or Firm* — Andrus Intellectual Property Law, LLP

(57) ABSTRACT

According to an exemplary embodiment, a method for processing an intraoral image comprises obtaining location data for an intraoral image target and processing an intraoral image in a predetermined manner on the basis of the intraoral image target's location data.

6 Claims, 2 Drawing Sheets

METHOD AND APPARATUS FOR PROCESSING AN INTRAORAL IMAGE

OBJECT OF THE INVENTION

The invention relates generally to a method and apparatus for processing an intraoral image.

PRIOR ART

In dental intraoral imaging, the thickness and density of an imaged target, i.e. the teeth, vary to a great extent according to which part of the dentition is being imaged. In molar regions, the teeth and jawbone have a thickness which considerably exceeds for example that of the frontal area, the attenuation of X-radiation and the change of its spectrum being different in these areas. Therefore, the resulting X-ray image is different unless the imaging values of an X-ray source or the properties of an image receptor are changed accordingly.

In intraoral imaging, the traditionally employed image receptor has been an X-ray film placed in the mouth, which has enabled imaging various dental regions by providing the X-ray source, which functions as an imaging apparatus, with different imaging values for different dental regions. In more sophisticated X-ray sources, the relevant imaging values can be programmed in a memory, whereby the imaging values for use in imaging can be selected from among graphic symbols matching the patient size and the imaged tooth in order to avoid over- or underexposure. This results in readable radiographs that can be examined by means of a dental chart as disclosed for example in patent publication U.S. Pat. No. 5,179,579.

Intraoral radiography is increasingly becoming digital, the X-ray film as an image receptor being replaced with an electronic photosensitive image sensor coupled to a scintillator, for example a CCD or CMOS semiconductor sensor, for which the received X-radiation is converted by the scintillator into appropriate light. An alternative for the scintillator is a semiconductor, which converts X-radiation directly into an electrical signal. Another alternative for the X-ray film is an image plate used in digital imaging, wherein the atoms become excited in response to X-radiation impinged thereon and for example a laser reader is used for reading an image stored on the image plate. A benefit of digital radiography is that the X-ray image produced therein can be corrected also afterwards, whereby the imaging process is not as exacting in terms of the employed imaging values.

In certain imaging systems, the image is often adjusted automatically in terms of its brightness and contrast and such systems are capable of producing useful X-ray imagery of the entire dental arch with the same imaging values of an X-ray source. Despite automatic adjustment, the X-ray images produced with the same imaging values nevertheless show small differences depending on the target being imaged and the size of a patient, whereby the X-ray images require subsequent manual adjustment in order to provide high quality X-ray images.

SUMMARY

One objective of the invention is to obviate some of the above drawbacks and to present a method of image processing intended for intraoral imaging.

One objective of the invention is achieved by a method of claim 1, one objective by an apparatus of claim 7, one objective by a system of claim 8, and one objective by a computer program of claim 9.

According to one embodiment of the invention, the method for processing an intraoral image comprises receiving location data for an intraoral image target and processing the intraoral image in a predetermined manner on the basis of the location data for the intraoral image target.

The term "location data" refers for example to data relating to a target area of intraoral imaging, for example a patient's dentition, of which the intraoral image is to be captured or of which the intraoral image has already been captured.

The term "predetermined" refers for example to the fact that, regarding intraoral image processing, the way of processing an image of the particular area, for example a dental area, has been determined prior to capturing the intraoral image.

According to one embodiment of the invention, an apparatus, for example a computer, a telephone, or some other display-equipped data processing device, for processing an intraoral image, is adapted to receive location data for an intraoral image target and to process the intraoral image in a predetermined manner on the basis of the location data for the intraoral image target.

According to one embodiment of the invention, a system, comprising for example at least an image processing computer, for processing an intraoral image, is adapted to receive location data for an intraoral image target and to process the intraoral image in a predetermined manner on the basis of the location data for the intraoral image target.

According to one embodiment of the invention, a computer program for processing an intraoral image comprises a code which is adapted to receive location data for an intraoral image target, and a code which is adapted to process the intraoral image in a predetermined manner on the basis of the received location data for the intraoral image target as the computer program is executed by a processor.

The method according to embodiments of the invention enables a simplification of intraoral image processing as each part of the dentition to be imaged in intraoral radiography can be subjected to optimal image processing measures automatically without specific procedures by the operator.

In addition, the method according to embodiments of the invention enables improving the quality and readability of an automatically obtained intraoral image.

Moreover, the method according to embodiments of the invention enables expediting the working process of imaging as the slow manual post-processing of images is omitted, and at the same time improving the average clinical quality of X-ray images.

Other embodiments of the invention are presented in the dependent claims.

DESCRIPTION OF FIGURES

Preferred embodiments of the invention will be explained slightly more specifically in the detailed description of figures with reference to the accompanying figures, in which.

DETAILED SPECIFICATION OF FIGURES

Figure 1:
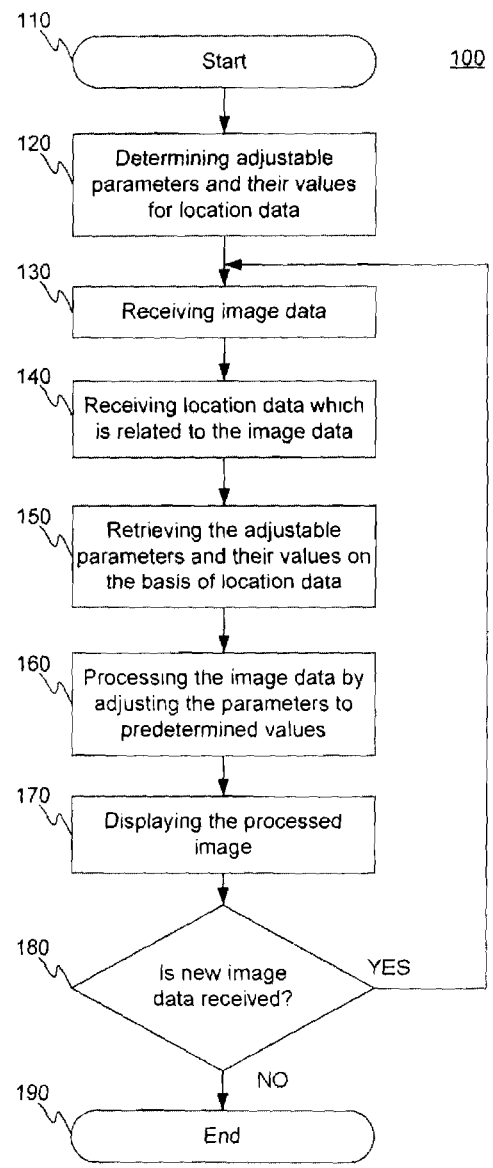
FIG. 1 shows an exemplary flow chart for a method of the invention.

FIG. 1 shows one method of the invention for processing an intraoral image, wherein the operator in a starting phase 110 switches on a computer intended for image processing and a computer program intended for image processing.

In a phase 120, the operator determines him-/herself or retrieves for example from a native database maintained by the computer, or from an available database maintained by some other computer, imaging parameters and/or image processing parameters applicable for example to all maxillary and mandibular teeth as well as to anterior and posterior teeth, and imaging values for the imaging parameters and/or values for the image processing parameters for use therein. The adjustable imaging parameters and/or image processing parameters, and the imaging values for imaging parameters and/or the values for image processing parameters, determined for each dental area, are stored either in the computer's native memory or in another computer which is in communication with the computer for example over an internal or external network in a manner to be retrievable therefrom as necessary. The adjustable image processing parameters include for example noise, brightness, contrast, resolution of contrast, spatial resolution, dynamic range, blur, artifacts, distortion, hue, saturation, intensity, red, green, and blue.

The adjustments of preset radiographic imaging values provide an influence for example on noise by setting the radiation dose of an X-ray apparatus used in imaging so as not to over- or underexpose the resulting image, thereby making sure that the image is readable. On the other hand, the adjustments of image processing parameters are used for adjusting the image depending on an imaged target, i.e. of which tooth or teeth the image has been captured, in an effort to improve the image in terms of its quality and readability.

After phase 120, or optionally before, in case the imaging values need not be determined, or at the same time, a patient for intraoral imaging is positioned so as to enable the patient to be imaged with an X-ray apparatus, and in the patient's mouth is placed an image sensor, for example a CCD or CMOS sensor, or an image plate, for use as an image receptor. When everything is set for imaging, an X-ray image is captured of the patient by using predetermined imaging values depending on which dental area is imaged and on the size of a patient in question.

In case the employed image receptor is an image sensor, which is connected for example over a cable link and/or a wireless link to an image processing computer, the resulting X-ray image data is communicated by means of the link to the computer used in image processing, which receives the X-ray image data in a phase 130. Alternatively, if the receptor comprises an image plate, the image plate is transferred to an image plate reader, in which the image plate content is read and the image data is conveyed for example over a cable link or a wireless link to the image processing computer. On the other hand, the operator of an image processing computer may also retrieve from the image processing computer's native memory, from the memory of another computer in communication with the image processing computer, or from an external memory, for example from a USB flash drive or an external hard drive, image data acquired and stored earlier therein.

In a phase 140, the image processing computer receives location data regarding a target of the intraoral image. The image processing computer contains one or more image processing programs, which enable the operator to examine an individual intraoral image and/or a dental chart made up by several intraoral images (image locations), including for example image locations for all anterior and posterior teeth, both from above and below. The dental chart (Full Mouth Series, FMS/FMX) comprises for example 18 image locations that cover the entire dentition.

The reception of location data may take place for example by reading a piece of location data included in the image data of an intraoral image, in the image plate or in the tag of an image plate, or by way of a control command given by the operator by way of the image processing computer's user interface, which command may comprise for example writing location data or image location data in the image data, a storage command for storing the intraoral image in a correct image location on the dental chart, or by picking up with the cursor a received intraoral image and by transferring the same to a correct spot (image location) on the dental chart, whereby the transferred intraoral image is stored in the image location automatically or in response to a separate storage command.

Alternatively, the location data can be obtained by way of the image processing computer's user interface even before the formation of an intraoral image, provided that the image processing computer functions as a remote controller for the X-ray apparatus over a cable communication or a wireless communication. Hence, at the same time as the operator-issued control command, which determines for an X-ray imaging apparatus the location of a target to be imaged, which is a rough location compared to location data required by the image processing program, and at the same time determines some of the imaging values used for this particular target, is communicated to the X-ray apparatus, the image processing program receives this rough information about the target of an intraoral image to be captured. Said control command is given by means of the push buttons of an X-ray imaging apparatus control unit's above-mentioned user interface and the control command contains rough information about a target, determining whether the question is for example about an anterior or posterior tooth. In addition, the operator is required by a further command to make it clear for the image processing program whether, for example in the case of a posterior tooth to be imaged, this particular posterior tooth is on the left or on the right.

On the other hand, the location data may come over a cable link and/or a wireless link directly from an X-ray imaging apparatus, which transmits the location data to an image processing computer after receiving a control command given by the X-ray apparatus operator through a user interface of the X-ray apparatus, which command indicates for the X-ray apparatus a rough location of the target to be imaged, and at the same time imaging values used for this particular target, as well as an additional command which makes the rough location data more accurate. Alternatively, the operator may issue to the X-ray apparatus a separate control command, which defines precisely the target location data, i.e. whether the question is about a left- or right-side anterior or posterior tooth, to be transmitted to an image processing program which is sent to the image processing computer.

As pointed out to some extent above, the phases 130 and 140 may also occur in reverse order or concurrently.

According to one embodiment, the invention relates to a method, which is presented in the foregoing embodiment and which comprises receiving a control command given by the operator to an image processing program directly through a user interface of the device running said program, which command indicates to a program intended for processing an intraoral image, an image location present in the program and matching an intraoral image formed of the target, i.e. an image target, receiving location data for the intraoral image target from an external device, for example from an X-ray imaging apparatus or an image plate reader, for example over a wired or wireless communication link, or reading an intraoral image target's location data included in the image data from among the information attached to the intraoral image.

According to one embodiment, the invention relates to a computer program, which is presented in the foregoing embodiment and which comprises a code adapted to receive a control command given by the operator to an image processing program directly through a user interface of the device running said program, which command indicates to a program intended for processing an intraoral image, an image location present in the program and matching an intraoral image formed of the target, i.e. an image target, a code adapted to receive location data for the intraoral image target from an external device, for example from an X-ray imaging apparatus or an image plate reader, for example over a wired or wireless communication link, or a code adapted to read an intraoral image target's location data included in the image data from among the information attached to the intraoral image.

According to one embodiment, the invention relates to a method, which is presented in any of the preceding embodiments and which comprises receiving from an intraoral image producing X-ray imaging apparatus a control command given by operator of the X-ray imaging apparatus, which control command indicates to a program intended for processing intraoral images, an image location present in the program and matching an intraoral image formed of the target, i.e. an image target.

According to one embodiment, the invention relates to a computer program, which is presented in any of the preceding embodiments and which comprises a code adapted to receive from an intraoral image producing X-ray imaging apparatus a control command given by operator of the X-ray imaging apparatus, which control command indicates to a program intended for processing intraoral images, an image location present in the program and matching an intraoral image formed of the target, i.e. an image target.

According to one embodiment, the invention relates to a method, which is presented in any of the preceding embodiments and which comprises storing a formed intraoral image in an image location in a program intended for processing intraoral images, said image location matching the intraoral image target's location data obtained on the basis of a received control command.

According to one embodiment, the invention relates to a computer program, which is presented in any of the preceding embodiments and which comprises a code adapted to store a formed intraoral image in an image location in a program intended for processing intraoral images, said image location matching the intraoral image target's location data obtained on the basis of a received control command.

In a phase 150, the image processing program retrieves, on the basis of location data received thereby, the adjustable image processing parameters and their values, said parameters having been determined for a particular dental area and stored for example in an image processing computer's native memory or in another computer in communication with the computer for example over an internal or external network.

According to one embodiment, the invention relates to a method, which is presented in any of the preceding embodiments and which further comprises retrieving, on the basis of an intraoral image target's received location data, at least one predetermined image processing parameter value for use in the processing of an intraoral image.

According to one embodiment, the invention relates to a computer program, which is presented in any of the preceding embodiments and which further comprises a code adapted to retrieve, on the basis of an intraoral image target's received location data, at least one predetermined image processing parameter value for use in the processing of an intraoral image.

Once the predetermined adjustable image processing parameters and their values have been retrieved, the formed and received intraoral image is processed in a phase 160 by adjusting predetermined image processing parameters, for example noise, brightness, contrast, resolution of contrast, spatial resolution, dynamic range, blur, artifacts, distortion, hue, saturation, intensity, red, green, and blue, such that the values thereof correspond to the predetermined and stored values of image processing parameters, and by presenting the processed image on the display of an image processing computer in a phase 170.

According to one embodiment, the invention relates to a method, which is presented in any of the preceding embodiments and which comprises processing an intraoral image in accordance with at least one predetermined image processing parameter value.

According to one embodiment, the invention relates to a computer program, which is presented in any of the preceding embodiments and which comprises a code adapted to process an intraoral image in accordance with at least one predetermined image processing parameter value.

If, in a phase 180, the image processing computer receives image data or location data regarding a new intraoral image, a return is made to the phase 130.

Otherwise, the method terminates in a phase 190.

Figure 2:
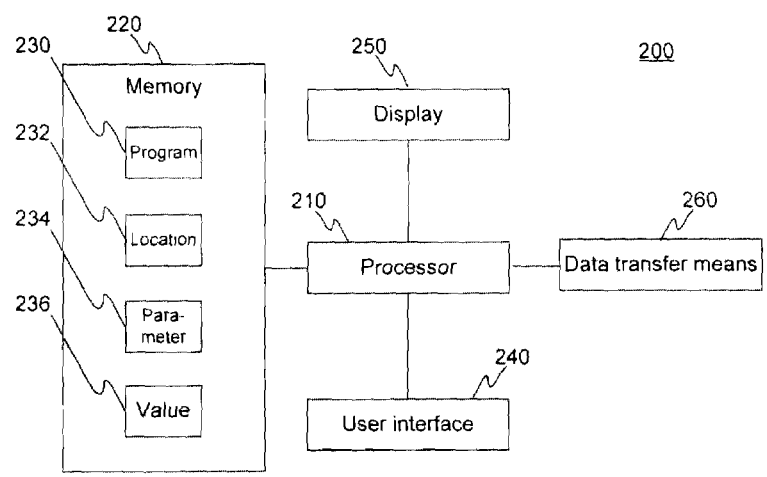
FIG. 2 shows an exemplary representative view of an apparatus of the invention.

FIG. 2 presents an image processing computer 200 according to one embodiment of the invention, which has a capability of processing an intraoral image.

The image processing computer 200 comprises a processor 210, or several processors, which enables executing instructions determined for example by the operator or an application program, and processing data. The image processing computer 200 has naturally an internal or external memory 220 for storing and maintaining data, for example instructions and user information, one or more image processing programs 230, dental location data 232, imaging parameters and/or image processing parameters 234, and the imaging parameters' imaging values and/or the image processing parameters' values 236. The image processing computer may also have several memories 220, all of which are for example internal or external memories or some of the memories are internal and some external.

The image processing computer 200 further comprises a user interface 240, for example a keyboard, a locator (mouse), a touch display, and/or a touchpad, enabling the user to input instructions and data to the image processing computer 200, a display 250 and a data transfer unit 260 for receiving and transmitting data over a cable communication link or a wireless communication link, The image processing program 230 present in the image processing computer's memory 220, along with the processor 210, provides a capability of executing a method according to one embodiment of the invention in the image processing computer 200.

According to one embodiment, the invention relates to an apparatus, which is presented in the foregoing embodiment and which is adapted to receive, for example by means of a processor, a data transfer unit, and/or a user interface, a control command given by the operator to an image processing program directly through a user interface of the device running said program, which command indicates to a program intended for processing an intraoral image, an image location present in the program and matching an intraoral image formed of the target, i.e. an image target, to receive location data for the intraoral image target from an external device, for example from an X-ray imaging apparatus or an image plate reader, for example over a wired or wireless communication link, or to read an intraoral image target's location data included in the image data from among the information attached to the intraoral image.

According to one embodiment, the invention relates to an apparatus, which is presented in any of the foregoing embodiments and which is adapted to receive, for example by means of a processor, a data transfer unit, and/or a user interface, from an intraoral image producing X-ray imaging apparatus a control command given by the X-ray imaging apparatus operator, which control command indicates to a program intended for processing intraoral images, an image location present in the program and matching an intraoral image formed of the target, i.e. an image target.

According to one embodiment, the invention relates to an apparatus, which is presented in any of the foregoing embodiments and which is adapted to store, for example by means of a processor, a memory and/or a user interface, a formed intraoral image in an image location in a program intended for processing intraoral images, said location corresponding to the location data of an intraoral image target obtained on the basis of a received control command.

According to one embodiment, the invention relates to an apparatus, which is presented in any of the foregoing embodiments and which is adapted to retrieve, for example by means of a processor, a memory and/or a data transfer unit, at least one predetermined image processing parameter value for use in the processing of an intraoral image on the basis of an intraoral image target's obtained location data.

According to one embodiment, the invention relates to an apparatus, which is presented in any of the foregoing embodiments and which is adapted to process, for example by means of a processor and/or a memory, an intraoral image in accordance with at least one predetermined image processing parameter value.

Figure 3:
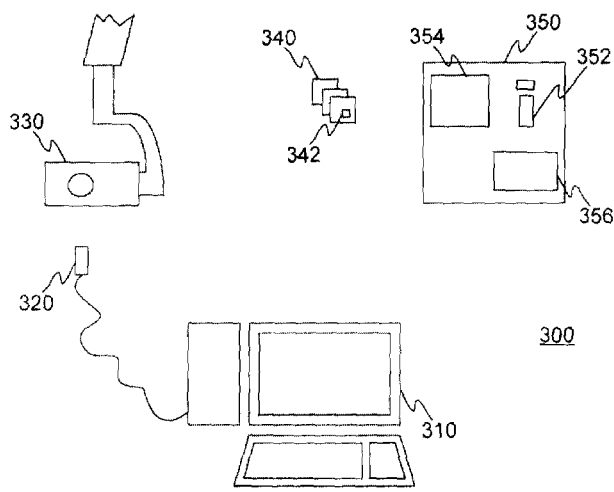
FIG. 3 shows an exemplary representative view of certain systems of the invention, making use of an image sensor useful in intraoral imaging, as well as image plates and an image plate reader.

FIG. 3 shows a system 300 according to one embodiment of the invention, which makes use of a digital image sensor, for example a CCD or CMOS sensor, or image plates and a reader of image plates.

The system 300 includes an image processing computer 310 similar to that shown in the previous figure, which contains for example a processor, a memory which has stored therein at least one image processing program, imaging parameters and/or image processing parameters, and imaging values for the imaging parameters and/or values for the image processing parameters, a user interface, a display, a data transfer unit, and one or more image sensors 320 in communication with the image processing computer 310 over the data transfer unit.

The system 300 may further include an X-ray imaging apparatus 330 used for intraoral radiography, which can be in communication with the image processing computer 310 over a cable link and/or a wireless link. In FIG. 3, the X-ray imaging apparatus communicates and receives information over a wireless link.

One way of implementing the system 300 is for example such that the operator gives the X-ray imaging apparatus 330, which comprises not only an X-ray imaging unit but also for example at least one processor, memory, user interface and data transfer means, over the X-ray apparatus' own user interface, imaging-related control commands, for example an imaging command, a control command containing for example rough location data for an imaging target and/or imaging parameters' imaging values which depend on the imaging target and are used in imaging, and/or a separate additional command making the rough location data more accurate, and/or an imaging command, which at the same time activates imaging and contains for example the imaging target's rough location data and/or the imaging parameters' imaging values which depend on the imaging target and are used in imaging and/or precise location data for a separate target to be imaged. In case the X-ray imaging apparatus 330 does not obtain useful imaging parameters along with a control command, but only receives rough location data in the control command, said apparatus, prior to activating the imaging process, retrieves valid imaging parameters either from its own database or from an external database by means of a cable link or a wireless link.

Upon receiving from the operator one or more control commands determining location data for an imaging target, the X-ray imaging apparatus 330 transmits, on the basis of one or more control commands, to the image processing computer 310, which manages an image processing program intended for processing intraoral images, the location data for an imaging target, and the image processing computer 310 searches the image processing parameters and their values used for processing images of this particular dental location.

Another option for implementing the system 300 is such that the image processing computer 310 functions as a remote controller for the X-ray imaging apparatus 330, whereby the imaging-related control commands are communicated by way of a presently employed communication link to the X-ray imaging apparatus 330, which, in addition to an X-ray imaging unit, comprises for example at least one processor, memory and data transfer means, and which executes imaging on the basis of instructions received thereby. The instructions may include for example a rough location for the imaging target and/or the imaging parameters' imaging values which depend on the imaging target and are used in imaging. In case the X-ray imaging apparatus 330 does not obtain useful imaging values along with a control command, but only receives a rough target location in the control command, said apparatus retrieves valid imaging values either from its own database or from an external database by means of a cable link or a wireless link.

Concurrently with sending a control command to the X-ray imaging apparatus 330, the image processing computer 310, functioning as a remote controller, will be able, on the basis of the transmitted control command and an operator-issued additional command required by an image processing program and making the rough location more accurate, to determine location data for the imaging target and to retrieve the image processing parameters and their values used for images of this particular dental location.

The image processing computer 310 may obtain location data required thereby also for example directly from the operator by way of its own user interface and/or by way of image data communicated by an image sensor 320 and/or from the actual image data, as already pointed out in the context of previous figures.

Alternatively, the image receptors employed in intraoral radiography are image plates 340, which may comprise for example a tag (RFID tag) 342 readable over a short range radio link, and which, after an imaging process, are read in an image plate reader 350 which is in communication with the image processing computer 310 over a cable link or a wireless link, as shown in the figure. The image plate reader 350 comprises at least one processor, a memory, an image plate insertion slot 352, a user interface, a display 354, a gutter-shaped image plate collector 356, and possibly a reader for the tags. In case the display 354 is a touch display, a separate user interface is not absolutely necessary.

When provided with the image plates 340 and the reader 350 for image plates, the system 300 can be implemented in such a way that the operator stores location data for an image target, i.e. the dentition, in the image plate's tag 342. This particular location data is read, along with an image contained in the image plate 340, in the image plate reader 350 and is transmitted, along with image data to be processed, over a cable link or a wireless link to the image processing computer 310 which, on the basis of said location data, retrieves the image processing parameters and their values used for processing images of this particular spot in this particular dentition, and processes the image data according to the values of the retrieved image processing parameters, such that its readability and quality are improved. Another possibility is that the reader operator feeds location data by way of a user interface into the reader 350, which transmits the location data either along with image data read from the image plate or separately to the image processing computer 310.

Alternatively, the image plate reader 350 is itself capable of managing an image processing program, processing the image data read thereby on the basis of location data, and transmitting over a cable link or a wireless link the processed intraoral images for utilization to other computers, by means of which other users are able to view and utilize the processed intraoral images or to present the same by means of their own display 354 and/or one or more external displays in communication with the image plate reader 350 over a cable link or a wireless link.

According to one embodiment, the invention relates to an apparatus, which is presented in the preceding embodiment and which is adapted to receive, for example by means of a processor, a data transfer unit and/or a user interface, a control command given by the operator to an image processing program directly through a user interface of the device running said program, which command indicates to a program intended for processing an intraoral image, an image location present in the program and matching an intraoral image formed of the target, i.e. an image target, to receive the location data for an intraoral image target from an external device, for example from an X-ray imaging apparatus or an image plate reader, for example over a wired or wireless link, or to read the location data for an intraoral image target included in the image data from among the information attached to the intraoral image.

According to one embodiment, the invention relates to an apparatus, which is presented in any of the preceding embodiments and which is adapted to receive, for example by means of a processor, a data transfer unit and/or a user interface, a control command from an intraoral image producing X-ray imaging apparatus given by the X-ray imaging apparatus operator, which control command indicates to a program intended for processing intraoral images, an image location present in the program and matching an intraoral image formed of the target, i.e. an image target.

According to one embodiment, the invention relates to an apparatus, which is presented in any of the preceding embodiments and which is adapted to store, for example by means of a processor, a memory and/or a data transfer unit, a formed intraoral image in an image location present in a program intended for processing intraoral images and matching the intraoral image target's location data obtained on the basis of a received control command.

According to one embodiment, the invention relates to an apparatus, which is presented in any of the preceding embodiments and which is adapted to retrieve on the basis of the obtained intraoral image target's location data, for example by means of a processor, a memory and/or a data transfer unit, at least one predetermined image processing parameter value for use in the processing of an intraoral image.

According to one embodiment, the invention relates to an apparatus, which is presented in any of the preceding embodiments and which is adapted to process, for example by means of a processor and/or a memory, an intraoral image in accordance with at least one predetermined image processing parameter value.

Presented above are but a few embodiments for a solution of the invention. The principle according to the invention can naturally be modified within the scope of protection defined by the claims, for example in terms of implementation details as well as operating areas.

The invention claimed is:

1. A method for processing intraoral images, said method comprising:
   obtaining first location data for a first intraoral imaging target area;
   obtaining an intraoral image of the first intraoral imaging target area;
   based on the first location data, selecting a first value of an adjustable image processing parameter;
   processing the intraoral image of the first intraoral imaging target area in a predetermined manner on the basis of the first value of the adjustable image processing parameter;
   obtaining second location data for a second intraoral imaging target area;
   obtaining an intraoral image of the second intraoral imaging target area:
   based on the second location data, selecting a second value of the adjustable image processing parameter, the second value being different from the first value; and
   processing the intraoral image of the second intraoral imaging target area in a predetermined manner on the basis of the second value of the adjustable image processing parameter.

2. A method according to claim 1, comprising receiving a control command, which indicates to a program intended for processing an intraoral image, an image location present in the program and matching an intraoral image formed of the target, receiving location data for an intraoral image target from an external device over a wired or wireless link or reading location data for an intraoral image target from among the information attached to an intraoral image.

3. A method according to claim 1, comprising receiving a control command from an intraoral image producing X-ray imaging apparatus, which control command indicates to a program intended for processing intraoral images, an image location present in the program and matching an intraoral image formed of the target.

4. A method according to claim 1, comprising storing a formed intraoral image in an image location, which is present in a program intended for processing intraoral images and which matches the intraoral image target's location data obtained on the basis of a received control command.

5. A method according, to claim 1, comprising retrieving, on the basis of the obtained intraoral image target's location data, at least one predetermined image processing parameter value for use in the processing of an intraoral image.

6. A method according to claim 5, comprising processing the intraoral image in accordance with the value of at least one predetermined image processing parameter.

* * * * *